United States Patent [19]

Mais et al.

[11] Patent Number: 5,679,826
[45] Date of Patent: Oct. 21, 1997

[54] PROCESS FOR THE PREPARATION OF 2-CHLOROACRYLONITRILE

[75] Inventors: Franz-Josef Mais, Düsseldorf; Thomas Essert, Overath; Helmut Fiege, Leverkusen; Friedrich Dürholz, Remscheid; Guido Steffan, Odenthal, all of Germany

[73] Assignee: Bayer Aktiengesellschaft, Leverkusen, Germany

[21] Appl. No.: 735,717

[22] Filed: Oct. 23, 1996

[30] Foreign Application Priority Data

Oct. 30, 1995 [DE] Germany ............... 195 40 358.4

[51] Int. Cl.$^6$ ............................................... C07C 253/30
[52] U.S. Cl. ............................................... 558/380; 348/461
[58] Field of Search ............................ 538/380, 461

[56] References Cited

U.S. PATENT DOCUMENTS

| | | | |
|---|---|---|---|
| 2,298,739 | 10/1942 | Lichty | 558/461 |
| 4,418,018 | 11/1983 | Kuroda et al. | 558/461 |

FOREIGN PATENT DOCUMENTS

| | | |
|---|---|---|
| 30869 | 6/1981 | European Pat. Off. |
| 1064502 | 9/1959 | Germany |
| 1076673 | 3/1990 | Germany |
| 56-87548 | 7/1981 | Japan |
| 87548 | 7/1981 | Japan |
| 831050 | 3/1960 | United Kingdom |

OTHER PUBLICATIONS

A. Lorette, J. Org. Chem. vol. 26, pp. 2325 to 2327 (1961).

H. Brintzinger, et al., Angew. Chem. A., vol. 60, pp. 311 to 312 (1948).

Patent Abstracts of Japan, vol. 6, No. 261, Abstract of JP 57 154 156 (1982).

*Primary Examiner*—Robert W. Ramsuer
*Attorney, Agent, or Firm*—Sprung Horn Kramer & Woods

[57] ABSTRACT

2-Chloroacrylonitrile is prepared in a particularly advantageous and readily industrially practicable manner by chlorinating acrylonitrile and then thermally cleaving the 2,3-diehloropropionitrile formed, by chlorinating acrylonitrile in the presence of a catalyst system comprising dimethylformamide and pyridine and/or pyridine derivatives and subjecting the resulting crude 2,3-dichloropropionitrile to thermal cleavage in the presence of the same catalyst system without the addition of further catalysts.

10 Claims, No Drawings

PROCESS FOR THE PREPARATION OF 2-CHLOROACRYLONITRILE

The present invention relates to a process for the preparation of 2-chloroacrylonitrile by addition of elemental chlorine onto acrylonitrile and subsequent thermal cleavage of the 2,3-dichloropropionitrile formed.

2-Chloroactylonitrile is a valuable intermediate in, for example, the preparation of plant protection products (see e.g. U.S. Pat. No. 5 145 986).

The preparation of 2,3-dichlompropionitrile by adding chlorine onto acrylonitrile is known. U.S. Pat. No. 2 390 470 describes the direct chlorination of acrylonitrile with chlorine under the action of light, in which the yields of 2,3-dichloropropionitrile are 80% at best. DE-A 1 568 161 claims this reaction with additives of, for example, hydrogen phosphates. However, good yields of more than 90% are achieved only at reaction temperatures of not more than 0° C. In addition, the heterogeneous inorganic constituents of the reaction mixture must be removed by filtration prior to subsequent use, and a polluted inorganic waste is obtained.

U.S. Pat. No. 2 429 031 describes the chlorination of acrylonitrile in the presence of catalytic amounts of hydrogen chloride. However, the results obtained in this experiment were misinterpreted, since in the presence of free hydrogen halide the principal product is 2,2,3-trichloropropionitrile.

Angew. Chem. 60, 311 to 312 (1948) describes the chlorination of acrylonitrile in the presence of pyridine as catalyst. The subsequent processing of the resulting 2,3-dichloropropionitrile to 2-chloroacrylonitrile is likewise described. For this purpose, however, the 2,3-dichloropropionitrile must first be distilled. The yield stated therein, of 95% for 2,3-dichloropropionitrile, was not able to be confirmed when this reaction was reworked (see J. Org. Chem. 26, 2325 to 2327 (1961)). The latter reference also describes the thermal cleavage of a crude, i.e. pyridine-containing, 2,3-dichloropropionitrile to give 2-chloroacrylonitrile. The yield of pure 2-chloroacrylonitrile, however, is only an unsatisfactory 60%. JP-A 56 087 548 claims the chlorination of acrylonitrile in the presence of acid amides, for example dimethylformamide, with distilled 2,3-dichlompropionitrile being obtained in a yield of 90%.

Numerous patent applications (EP-A 30 869, EP-A 59 033, JP-A 57-064 656, JP-A 57-254 156, JP-A 57-136 556 and JP-A 01-258 653) describe the chlorination of acrylonitrile to give 2,3-dichloropropionitrile in the presence of heterogeneous catalysts. Examples of the catalysts employed are alkali metal carbonates, alkali metal hydrogen carbonates, alkali metal hydrogen phosphates and dihydrogen phosphates, combinations of optionally substituted pyridine with alkali metal carbonates, and combinations of potassium carbonate with polyvinylpyridine. The yields are generally good, often over 95%, and the purities in the crude product are about 98%. The heterogeneous catalyst must be removed by filtration prior to further reaction, for example cleavage to 2-chloroacrylonitrile, and a highly polluted, solid waste is obtained which is difficult to dispose of. The crude product is subsequently distilled, in the course of which there is generally no cleavage into 2-chloroacrylonitrile (see e.g. EP-A 30 869, Example 2).

JP-A 56-100 754 describes the chlorination of acrylonitrile with the aim of the direct decomposition of the crude 2,3-dichloropropionitrile into 2-chloroacrylonitrile. The process, however, possesses grave disadvantages. The inorganic heterogeneous "catalyst" for the chlorination, generally alkali metal or alkaline earth metal hydrogen phosphate or dihydrogen phosphate, has to be employed in an mount of 120 mole %, based on acrylonitrile. Moreover, the reaction temperature must be maintained in the vicinity of 0° C.; in other words, the dissipation of the heat of reaction from the highly exothermic chlorine addition is expensive. The yield of 2-chloroacrylonitrile (after chlorination, thermal cleavage and distillation) is only 80.2% (70.2 g of 2-chloracrylonitrile from 53 g of acrylonitrile). The greatest disadvantage of this process, however, is the implementation of all of the process steps in the presence of a disproportionately large amount of phosphates. This leads, during the thermal cleavage and especially in the course of the final distillation, to severe bumping in the bottom of the reaction and distillation apparatus. In order to distill off the product the phosphate-containing residue must be evaporated to dryness, which is virtually impossible to carry out on an industrial scale.

Apart from the literature references already mentioned, the elimination of hydrogen chloride from 2,3-dichloropropionitrile is also known from several other publications. A very wide variety of reagents is described for the elimination of hydrogen chloride; for instance, U.S. Pat. No. 2 385 550 uses secondary and tertiary amines (85% yield distillation), DE-B 883 891 uses salts of polycarboxylic acids in an aqueous medium (there is no example of the cleavage of 2,3-dichloropropionitrile), U.S. Pat. No. 2 862 963 uses acidic reagents such as aromatic sulfonic acids and polymeric sulfonic-acid salts (Example 4, which relates to the cleavage of 2,3-dichloropropionitrile, gives no indication of yield), U.S. Pat. No. 2 870 192 uses concentrated sulfuric acid (see Example 2, but with no indication of the yield), U.S. Pat. No. 3 361 786 uses potassium fluoride (yield not more than 83.5%, see Table 3), and DE-A 1 768 807 and U.S. Pat. No. 3 845 095 use aqueous solutions of alkali metal hydrogen phosphates and alkali metal dihydrogen phosphates. The latter process, which is highly complex, gives a yield of 87.5% at best (Example 1 of DE-A 1 768 807) of a material obtained by phase separation from an aqueous phase. However, the 2-chloroacrylonitrile cannot be used industrially in this wet form, with the result that a laborious and yield-reducing drying operation is additionally required. GB-B 1 287 854 describes the elimination of hydrogen chloride with aqueous ammonia, the yield according to Example 2 being 80%.

DE-B 1 150 381 claims a process for the thermal cleavage of 2,3-dichloropropionitrile in the presence of iron, aluminum or chlorides thereof as catalysts. The yield of what is per se an advantageous process is, at 95%, good. However, it is necessary to employ pure 2,3-dichloropropionitrile which has been worked up intermediately beforehand and in which the chlorination catalysts are no longer present.

Finally, U.S. Pat. No. 2 231 363 describes a direct gas-phase process in which 2-chloroacrylonitrile can be obtained from acrylonitrile and chlorine from 200 to 500° C. in one step with the in situ generation and cleavage of 2,3-dichloropropionitrile. The yield is, however, only 40%.

Definite disadvantages of the cited prior art are that, in many processes, it is necessary following the chlorination of acrylonitrile to give 2,3-dichloropropionitrile to remove the catalyst (possibly with major disposal problems) and to purify the 2,3-dichloropropionitrile further by distillation. The pure 2,3-dichloropropionitrile can then be employed in the cleavage to form 2-chloroacrylonitrile. The few publications which describe the use of 2,3-dichloropropionitrile comprising crude catalysts or other reagents operate with unsatisfactorily low yields and are in some cases hardly practicable on the industrial scale.

There therefore continues to be a need for a simple process for the preparation of 2-chloroacrylonitrile in high yields which can also be carried out readily on an industrial scale.

A process has now been found for the preparation of 2-chloroacrylonitrile by chlorinating acrylonitrile and then thermally cleaving the 2,3-dichloropropionitrile formed, which comprises chlorinating acrylonitrile in the presence of a catalyst system comprising dimethylformamide and pyridine and/or pyridine derivatives and subjecting the resulting crude 2,3-dichloropropionitrile to thermal cleavage in the presence of the same catalyst system without the addition of further catalysts.

In the process according to the invention it is possible in the first stage (chlorination) to employ acrylonitrile which is commonly available commercially. Such acrylonitrile frequently comprises polymerization inhibitors, for example hydroquinone, hydroquinone monomethyl ether, phenothiazine, tert-butylated phenols and/or cresols in amounts of, for example, from 40 to 100 ppm. The presence of such amounts of polymerization inhibitors does not disrupt the process according to the invention. It is also possible to employ acrylonitrile comprising no polymerization inhibitors.

The first stage of the process according to the invention, the chlorination of acrylonitrile, can be carried out in the liquid phase with or without the addition of a solvent. Suitable solvents are those which are not attacked by chlorine under the reaction conditions, examples being carbon tetrachloride, perchloroethylene and other chlorinated hydrocarbons. Preferably, no solvent is added.

The chlorinating agent used can be gaseous chlorine. The amount of the chlorinating agent can be, for example, in the range from 0.9 to 1.1 mol per mole of acrylonitrile employed. This amount is preferably from 0.95 to 1.05 mol, in particular from 0.99 to 1.05 mol.

An essential feature of the process according to the invention is the use of a catalyst system comprising dimethylformamide (DMF) and pyridine and/or one or more pyridine derivatives. Dimethylformamide can be employed, for example, in an amount of from 0.1 to 20 mol %, based on acrylonitrile. This amount is preferably from 0.5 to 10 mol %, particularly preferably from 1 to 7.5 mol %.

The pyridine component can be employed, for example, in an amount of from 0.05 to 10 mol %, based on acrylonitrile. This amount is preferably from 0.1 to 7.5 mol %, particularly preferably from 0.5 to 5 mol %.

Pyridine and pyridine derivatives can each be employed alone or in any desired mixtures with one another. Pyridine and pyridine derivatives are also referred to in the following text, together, as pyridine component.

The pyridine component may, for example, comprise compounds of the formula (I)

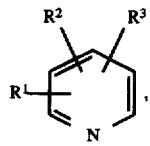

in which $R^1$, $R^2$ and $R^3$ independently of one another are each hydrogen, straight-chain, branched or cyclic $C_1$–$C_6$-alkyl, phenyl or benzyl and two of these radicals $R^1$, $R^2$ and $R^3$, if adjacent, can also together be a —(CH$_2$)$_3$— or —(CH$_2$)$_4$—group.

Straight-chain, branched or cyclic $C_1$–$C_6$-alkyl is, for example, methyl, ethyl, propyl, isopropyl, butyl, tert-butyl or cyclohexyl. Preferably, $R^1$, $R^2$ and $R^3$ independently of one another are each hydrogen, straight-chain or branched $C_1$–$C_4$-alkyl, phenyl or benzyl, particularly preferably hydrogen, methyl or ethyl.

The molar ratio of dimethylformamide to the pyridine component can, for example, be in a range from 20:1 to 0.5:1. This ratio is preferably from 10:1 to 1:1, in particular from 7.5:1 to 2:1.

The reaction temperature for the chlorination can, for example, be from 10° to 60° C. It is preferably from 20° to 50° C., especially from 25° to 45° C.

The chlorination can be carried out under atmospheric pressure, reduced pressure or elevated pressure. Preference is given to atmospheric pressure or a slight excess pressure resulting from the apparatus.

In accordance with the invention, no further catalyst is added to carry out the thermal cleavage of the crude 2,3-dichloropropionitrile.

The second stage of the process according to the invention (thermal cleavage) can likewise be carried out in the liquid phase. In this case it is possible to operate either in dilution with a solvent, preferably a high-boiling solvent, or else without the addition of a solvent. Suitable high-boiling solvents, which are not attacked under the reaction conditions by hydrogen chloride, acrylonitrile or chlorination products thereof, are, for example, polychlorobenzenes such as 1,2-dichlorobenzene and 1,2,4-trichlorobenzene, high-boiling mineral oils, polyethylene glycols with average molecular weights of, for example, from 300 to 400, dimethylformamide and N-methylpyrrolidone.

The thermal cleavage is preferably carried out without the addition of a solvent.

In order to avoid polymerization, under the conditions of thermal cleavage, of the 2-chloroacrylonitrile formed, it is possible to add a customary polymerization inhibitor to the cleavage mixture. Examples which may be mentioned are hydroquinone, hydroquinone monomethyl ether and phenothiazone.

In the cleavage reaction, it is possible to employ directly the reaction mixture comprising 2,3-dichloropropionitrile that comes from the chlorination of acrylonitrile. In the course of thermal cleavage the 2-chloroacrylonitrile formed and the hydrogen chloride formed distill off. The cleavage reaction can be performed, for example, at from 80° to 160° C., preferably from 90° to 140° C. and particularly preferably from 90° to 110° C. (in each case measured in the liquid phase). The thermal cleavage can be carried out under atmospheric pressure, reduced or elevated pressure. Preference is given to atmospheric pressure or a slight excess pressure resulting from the apparatus.

The process according to the invention can be performed in a variety of variants, exemplified by the following: the first stage of the process, the chlorination of acrylonitrile, can be carried out either continuously or batchwise. One exemplary embodiment is as follows: acrylonitrile is initially introduced into a chlorination vessel, the two catalyst components are added, and chlorine is passed in at the desired reaction temperature. After a brief period of stirring the material can either be employed directly for the cleavage reaction or stored in the interim. The second stage, the cleavage of the catalyst-containing 2,3-dichloropropionitrile, can likewise be performed in a variety of variants. Examples of exemplary embodiments are the following: the entire amount of the 2,3-dichloropropionitrile is initially introduced into a vessel and heated until cleavage begins. The products which form, 2-chloroacrylonitrile and hydrogen chloride, are passed over a short condenser. The condensate, which consists essentially of 2-chloroacrylonitrile, can be distilled again, if desired, for free purification.

Another embodiment is as follows: a portion of the crude 2,3-dichloropropionitrile is heated in a distillation still until cleavage begins. The 2-chloroacrylonitrile and the hydrogen chloride formed distill off, by way of a separation column which is mounted if appropriate. At the same rate, the remaining crude 2,3-dichloropropionitrile is metered into the liquid phase. At the end, post-heating is carried out briefly until the cleavage reaction subsides. Especially when a separating column is used, the 2-chloroacrylonitrile obtained is already of sufficient purity that it can be passed on for the known uses without further treatment. In particular, additional distillation is no longer necessary in this case.

An extremely surprising feature of the process according to the invention, which was not to be expected given the known prior art, is that a combination of dimethylformamide with pyridine components possesses a catalytic action for both stages and that a high yield can be realized both in the chlorination and in the thermal cleavage. That the 2,3-dichloropropionitrile need no longer be purified intermediately, and that the inorganic, highly polluting reagents requiring removal by filtration are no longer necessary, are major technical advances. The yields of 2-chloroacrylonitrile are high and, considered over both reaction stages, are generally from 85 to 95%.

The examples which follow illustrate the process according to the invention without restricting it to the embodiments set out therein.

EXAMPLES

Examples 1 to 6

2650 g of acrylonitrile were initially introduced into a chlorination beaker, which was protected against light, and the chlorination catalyst was added. Gaseous chlorine was metered in below the surface of the liquid with stirring. An exothermic reaction ensued. At the desired reaction temperature, a further increase in temperature was prevented by deploying an effective cooling system.

A total of 3550 g of chlorine were passed in over the come of 10 hours. The mixture was subsequently stirred at the reaction temperature for 1 hour more.

The reaction mixtures obtained could be fed directly into the cleavage reaction to form 2-chloroacrylonitrile and hydrogen chloride. The details and results of Examples 1 to 6 can be seen from Table 1.

TABLE 1

| Ex. Catalyst | Reaction Temperature | Mass of product | 2,3-Dichloropropionitrile GC purity | Yield |
|---|---|---|---|---|
| 1  3.5 mol % DMF, 5 mol % pyridine | 30° C. | 6515 g | 93.0% | 97.7% |
| 2  1 mol % DMF, 5 mol % pyridine | 30° C. | 6405 g | 94.2% | 97.3% |
| 3  1 mol % DMF, 7 mol % 2-methylpyridine | 40° C. | 6560 g | 92.8% | 98.2% |
| 4  3.5 mol % DMF, 4 mol % 2-phenylpyridine | 30° C. | 6640 g | 90.2% | 96.6% |
| 5  1 mol % DMF, 3.5 mol % 2-methylpyridine | 35° C. | 6380 g | 95.0% | 97.7% |

TABLE 1-continued

| Ex. Catalyst | Reaction Temperature | Mass of product | 2,3-Dichloropropionitrile GC purity | Yield |
|---|---|---|---|---|
| 6  1 mol % DMF, 3.5 mol % 2,4-dimethylpyridine | 35° C. | 6415 g | 94.9% | 98.2% |

Example 7

1312 g (10.0 mol) of the product from Example 3 were initially introduced into a 2000 ml multineck flask with mirror-coated 1 m Vigreux column mounted, and 10 g of hydroquinone were added. The mixture was heated with stirring until, at about 100° C., cleavage began, and stirring was then continued at from 125° to 130° C., in the course of which 2-chloroacrylonitrile and hydrogen chloride distilled off via the column. The hydrogen chloride was taken off at the head of the column via a condenser. The condensate was drawn off hot into the receiver at a reflux ratio of 1:1. The overhead temperature was 85° C. The yield of 99% pure 2-chloroacrylonitrile (GC) was 760 g. This corresponds to 86.9% over both reaction states.

Example 8

131 g (1.0 mol) of the product from Example 3 were initially introduced into a 500 ml multineck flask with mirror-coated 1 m Vigreux column mounted, and 5 g of hydroquinone were added. The mixture was heated with stirring at from 125° to 130° C. 2-Chloroacrylonitrile and hydrogen chloride distilled off via the column. The hydrogen chloride was taken off, as in Example 7, at the column head via a condenser. The 2-chloroacrylonitrile distillate was taken off hot at a reflux ratio of 1:1. The overhead temperature was 85° C. In the proportion in which 2,3-dichloropropionitrile was consumed from the liquid phase by cleavage, 1181 g (9.0 mol) of the product from Example 3 were metered in subsequently over the course of 10 hours. After a post-heating phase of 30 minutes at from 130° to 135° C., a total of 810 g of 2-chloroacrylonitrile with a purity of about 99% were obtained. This corresponds to a yield of 92.6% over both reaction stages.

Example 9

The process of Example 7 was repeated with 1281 g (10.0 mol) of the product from Example 2. 745 g (=85.1% over both reaction stages) of 98.5% pure 2-chloroacrylonitrile were obtained.

We claim:

1. A process for the preparation of 2-chloroacrylonitrile by chlorinating acrylonitrile and then thermally cleaving the 2,3-dichloropropionitrile formed, which comprises chlorinating acrylonitrile in the presence of a catalyst system comprising dimethylformamide and pyridine and/or pyridine derivatives and subjecting the resulting crude 2,3-dichloropropionitrile to thermal cleavage in the presence of the same catalyst system without the addition of further catalysts.

2. The process as claimed in claim 1, wherein dimethylformamide is employed in an amount of from 0.1 to 20 mol %, based on acrylonitrile.

3. The process as claimed in claim 1, wherein pyridine and pyridine derivatives is or are employed in an amount of from 0.05 to 10 mol %, based on acrylonitrile.

4. The process as claimed in claim 1, wherein pyridine and/or one or more pyridine derivatives of the formula (I) is or are employed

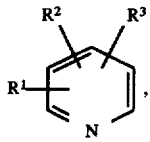 (I)

in which

R¹, R² and R³ independently of one another are each hydrogen, straight-chain, branched or cyclic $C_1$–$C_6$-alkyl, phenyl or benzyl and two of these radicals R¹, R² and R³, if adjacent, can also together be a —$(CH_2)_3$— or —$(CH_2)_4$—group.

5. The process as claimed in claim 4, wherein pyridine and/or one or more pyridine derivatives of the formula (I) is or are employed in which R¹, R² and R³ independently of one another are each hydrogen, straight-chain or branched $C_1$–$C_4$-alkyl, benzyl or phenyl.

6. The process as claimed in claim 1, wherein the chlorination of acrylonitrile is carried out at from 10° to 60° C.

7. The process as claimed in claim 1, wherein the chlorination of acrylonitrile is carried out with from 0.9 to 1.1 mol of chlorine per mole of acrylonitrile.

8. The process as claimed in claim 1, wherein the thermal cleavage of the crude 2,3-dichloropropionitrile is carried out at a temperature of from 80° to 160° C.

9. The process as claimed in claim 1, wherein the molar ratio of dimethylformamide to pyridine and/or pyridine derivatives is in the range from 20:1 to 0.5:1.

10. The process as claimed in claim 1, wherein the chlorination is carried out at from 20° to 50° C. and the cleavage at from 90° to 140° C.

* * * * *